United States Patent [19]

Ravetta

[11] Patent Number: 4,876,388
[45] Date of Patent: Oct. 24, 1989

[54] METHOD FOR THE PURIFICATION OF TRIFURALINE

[75] Inventor: Guido Ravetta, Milan, Italy

[73] Assignee: I.PI.CI. S.p.A., Novate, Italy

[21] Appl. No.: 196,880

[22] Filed: May 20, 1988

Related U.S. Application Data

[63] Continuation of Ser. No. 892,384, Jul. 31, 1986, abandoned.

[51] Int. Cl.⁴ .............................................. C07C 85/26
[52] U.S. Cl. ................................................... 564/437
[58] Field of Search ................................. 564/437, 441

[56] References Cited

U.S. PATENT DOCUMENTS

| | | | |
|---|---|---|---|
| 4,078,000 | 3/1978 | Gavin et al. | 564/437 |
| 4,120,905 | 10/1978 | Cannon et al. | 568/933 |
| 4,127,610 | 11/1978 | Eizember | 564/437 |
| 4,134,917 | 1/1979 | Ross et al. | 564/437 |
| 4,185,035 | 1/1980 | Eizember et al. | 564/437 |
| 4,266,789 | 10/1980 | Eizember et al. | 564/437 |
| 4,338,473 | 7/1982 | Habig et al. | 568/933 |

OTHER PUBLICATIONS

*Chemical Abstracts,* 73:62440j (1970).

*Primary Examiner*—Douglas W. Robinson
*Assistant Examiner*—Raymond J. Henley, III
*Attorney, Agent, or Firm*—Bernard, Rothwell & Brown

[57] ABSTRACT

Crude trifluralin is subjected to a purification treatment to remove nitrosamines therefrom and to improve its content of the active principle.

The treatment consists of passing through the trifluralin, kept in the liquid state at a temperature of from 50° to 110° C., a quantity of from 1 to 4 times its weight of saturated steam at 105° to 110° C.

The nitrosamine content of the treated trifluraline is less than 1 ppm.

8 Claims, No Drawings

METHOD FOR THE PURIFICATION OF TRIFURALINE

This is a continuation of application Ser. No. 892,384, filed July 31, 1986 now abandoned.

The present invention relates to a method for purifying trifluralin, in particular for removing therefrom any nitrosamines which may be present in small quantities.

Trifluralin is the commercial name used for the compound:

4-trifluoromethyl-2,6-dinitro-N,N-di-n-propylaniline, which is a compound widely used in agriculture as a herbicide.

After the development of highly-sensitive, analytical methods, such as those using, for example, thermal energy analysers(TEA) or mass spectrometer on eluates from chromatographic separation (GC/MS),to evaluate nitrosamines present even in trace quantities (less than 0.02 ppm) in nitroanilines (and hence also in trifluralin), it was possible to discover that some trifluralins contained nitrosamines in quantities of from a few ppm to several hundreds of ppm.

The origin of the nitrosamines in trifluralin was traced back to the process used for its preparation, when the final stage thereof consists of a reaction between di-n-propylamine and 4-trifluoromethyl-2,6-dinitro-chloro-benzene.

This latter compound may contain several nitroso-forming agents which react with the amine to give the nitrosamines.

The presence of nitrosamines in trifluralin, even in quantities of a few ppm, has been considered undesirable ever since the discovery of the carcinogenic activity of some nitrosamines in animals.

Various processes have thus been developed for eliminating nitrosamines from trifluralin or for avoiding the formation thereof by the prior treatment of the dinitro-derivatives to eliminate therefrom the nitroso-forming agents which can give rise to the formation of nitrosamines.

Thus, for example, it has been proposed to treat trifluraline with aqueous concentrated or gaseous hydrochloric acid (U.S. Pat. No. 4,226,789) or with inorganic acid chlorides such as $PCl_3$, $PCl_5$, $SOCl_2$, $TiCl_4$ (U.S. Pat. No. 4,185,035) or with bromine or chlorine (U.S. Pat. No. 4,127,610) or with hydrochloric acid or hydrobromic acid in the presence of ketones or aldehydes (U.S. Pat. No. 4,134,917).

All the methods mentioned destroy the nitrosamines and eliminate them from the trifluralin to residual levels of less than 1 ppm.

Other methods proposed in the art, such as, for example, in U.S. Pat. Nos. 4,120,905 and 4,338,473 are directed, instead, at the elimination of the nitroso-forming agents present in the dinitro-derivative used as the intermediate in the preparation of trifluralin and are based on the treatment of the intermediate with aqueous alkaline solutions with the simultaneous bubbling therethrough of inert gas such as air, or treatment with water which is at least partially distilled.

The aforementioned methods of treating trifluralin have the faults of requiring the addition of extraneous substances and of prolonged reaction times to ensure that the nitrosamines are destroyed to the desired levels while the methods used for treating the intermediate give no guarantee that the nitroso-forming agents will have been completely eliminated since there are no analytical methods for checking them and the certainty of their removal may be discovered only after the final product, trifluralin, has been prepared and tested analytically.

It has now been found that it is possible to remove both the nitrosamines and other possible impurities of an undefined nature from trifluralin by a much simpler and more effective method, without incurring the aforementioned disadvantages of the other methods.

According to the invention, nitrosamines and other organic impurities of an unknown nature present in some trifluralins may be removed by passing steam through the trifluralin in the liquid state.

In particular, saturated steam at a temperature of from 105° to 110° C. is passed through the trifluralin, kept in the liquid state at a temperature of between 50° and 110° C., the pressure being regulated so as to avoid substantial condensation of the steam in the reactor; the emission of steam is continued until a quantity of steam corresponding to from 1 to 4 times the weight of trifluralin, has been passed through the liquid trifluralin.

By trifluralin in the liquid state is meant trifluralin which is molten or dissolved in organic solvents such as, for example, aliphatic, cycloaliphatic, or aromatic hydrocarbons or their halogenated derivatives, ketones, aldehydes or ethers.

In the preferred embodiment, the method of the present invention is, however, carried out with the trifluralin in the molten state, without recourse to any added solvents.

In preferred embodiments of the invention, the steam is passed through the trifluralin while care is taken to avoid condensation thereof in the reactor: this does not mean, however, that partial condensation of the steam in the reactor alters or prevents the purification of the trifluralin.

Partial condensation of the steam in quantities of even up to 15% by weight of the weight of the trifluralin, do not affect the purity of the final product.

Any water in the reactor causes two liquid phases to form and, at the end of the steam treatment, the aqueous liquid phase may be separated from the purified trifluralin simply by decantation or heating of the reaction mass until the aqueous phase has evaporated completely.

When solvents have been used to dissolve the trifluralin to be purified, the solvents are recovered by distillation or by separation from the water obtained by condensation of the steam used to treat the trifluralin.

The fact that it is possible to separate the nitrosamines present in some trifluralins, by using the steam treatment of the present invention is rather surprising in that it is absolutely impossible to separate nitrosamines by distillation at the same temperatures, even when very low operating pressures (down to 1 mbar) are used.

Nor is it possible to separate the nitrosamines by repeated washing with water, even at temperatures up to 100° C.

With the process of the present invention, however, practically complete separation of nitrosamines from trifluralin (down to quantities of less than 1 ppm) is achieved and, furthermore, other impurities which have not yet been fully identified, but which are present in the trifluralin, are also removed, giving a considerable improvement in the content of the useful product.

Without wishing to bind the present invention to a particular interpretive mechanism, it is thought that the nitrosamines and other impurities which are removed by the method of the present invention are dissolved in the trifluralin in forms in which they are highly solvated by the trifluralin itself but, in any case, such as to make it impossible to remove them by distillation or washing with water.

On the other hand it is not possible to raise the distillation temperature above 130° C. since, even at this temperature, incipient decomposition of the trifluralin is noted, with the formation of byproducts which lower the content of the product instead of improving it. These difficulties occur since, in the art, methods have been developed for the elimination of the nitrosamines by reaction of the said impurities with particular reagents instead of methods for their separation from the trifluralins, containing them.

The best method of carrying out the method according to the present invention consists of melting the crude trifluralin in a reactor and bringing the temperature of the melt to between 90° and 105° C. When this temperature has been reached, saturated steam is passed into the liquid mass at a temperature of between 105° and 110° C. and the steam which has passed through the liquid mass is removed from the reactor.

The emission of steam is continued until a quantity of steam of from 2 to 4 times the weight of the liquid treated has been passed through the liquid mass.

The steam and the substances entrained therein are condensed by cooling, two immiscible liquid layers thus being obtained, an organic one containing most of the impurities and an aqueous one.

The organic layer, after separation from the aqueous layer is destroyed by combustion while the aqueous layer is sent for purification of the return water.

The quantity of the organic substances separated from the crude trifluralin and contained essentially in said organic layer, is from 1 to 3% by weight of the crude trifluralin treated.

Typically, if the method is carried out as described, improvements in the active-principle content are obtained which are greater than 1% with respect to the content in the crude, starting trifluralin.

The method is particularly advantageous in the case of crude trifluralins which have a lower content than that normally required in that it allows the content of the purified product to be raised to the required level.

While, in order to purify crude trifluralins with contents of more than 95% by weight, it suffices to use quantities of steam within the limits mentioned above, when it is necessary to treat crude trifluralins with contents of less than 95%, greater quantities of steam must be used.

The most suitable quantity of steam in the latter cases will, however easily be determined by the expert in the art from a simple check on the quantity of organic substances separated by condensation of the steam leaving the reactor. The emission of steam into the reactor will be stopped when no further separation of substances by condensation of the steam leaving the reactor is noted.

The following examples serve to illustrate the present invention better, without in any way limiting it.

The analyses for the nitrosamine determinations were all effected by mass spectrometry on the eluates resulting from chromatographic separation and subsequent concentration by the Kuderna-Danish apparatus.

EXAMPLE 1

200g of crude trifluralin (96.6% content) with a nitrosamine content of 11.1 ppm were placed in a 750 ml glass flask having an agitator, an inlet aperture, an inlet tube opening into the bottom of the flask for the emission of steam and an outlet aperture for the steam equipped with a splash preventer.

The trifluralin in the flask was heated to 100° C. and then the emission of saturated steam at 105° C. through the inlet tube was started. The steam leaving the flask was passed through a water condenser and the condensate was collected in a separator funnel. The operation was carried out at atmospheric pressure. The emission of steam was continued until 800 ml of an aqueous layer and about 3 ml of an organic layer had collected in the separator funnel.

The emission of steam was then stopped and the heating of the material in the flask was continued until all the water had been removed, the temperature being brought to 105° C. After cooling, the product in the flask was analysed and found to have a trifluralin content of 98.2% and a nitrosamine content of 0.3 ppm.

EXAMPLE 2

This was carried out as in Example 1 except that the emission of steam was stopped when 600 ml of water had collected in the separator funnel.

The quantity of the organic layer was about 2 ml.

The trifluralin content of the purified product was 97.8% and its nitrosamine content was 0.9 ppm.

EXAMPLE 3

This was carried out as in Example 1 except that crude trifluralin with a trifluralin content of 96.5% and a nitrosamine content of 27ppm was treated.

The emission of steam was stopped when the water collected in the separator funnel reached 400 ml.

The trifluralin treated had a nitrosamine content of 0.3 ppm and a trifluralin content of more than 97%.

EXAMPLE 4

200 g of crude trifluralin having a nitrosamine content of 2.4 ppm dissolved in toluene (200 g) were placed in the flask used for Example 1.

The solution was heated to 90° C and saturated steam at 103° C. was passed into the solution. The emission was continued until all the toluene used to make the solution (200 g) had collected in the separator funnel.

The analysis of the trifluralin remaining in the flask showed a nitrosamine content of 0.3 ppm.

EXAMPLE 5

Example 4, was repeated, the crude trifluralin being dissolved in 200 g of methyl ethyl ketone instead of toluene.

The treated trifluralin, had a nitrosamine content of 0.3ppm.

EXAMPLE 6

Example 4 was repeated but solvents were not used and the crude trifluralin, was simply melted at 90° C. and then treated with the saturated steam at 103° C.

The emission of steam was stopped when 400 ml of water had collected in the separator funnel.

The treated trifluralin had a nitrosamine content of 0.3 ppm

I claim:

1. A method of purifying trifluralin, which comprises:

passing saturated steam at a temperature of from 105° to 110° C. through the trifluralin, kept in the liquid state at a temperature of from 50° to 110° C., the pressure being regulated so as to avoid substantial condensation of the steam in the reactor;

continuing the emission of steam until a quantity of steam corresponding to from 1 to 4 times the weight of the trifluralin has been passed through the liquid trifluralin; and recovering the purified trifluralin after the removal of any aqueous phase which may have formed during the treatment with the steam.

2. Method as claimed in claim 1, wherein the liquid trifluralin is molten trifluralin.

3. Method as claimed in claim 1, wherein the liquid trifluralin is trifluralin dissolved in an organic solvent.

4. Method as claimed in claim 1, wherein the quantity of steam which condenses in the reactor is less than 15% by weight of the quantity of trifluralin in the liquid state.

5. Method as claimed in claim 1, wherein the temperature of the trifluralin in the liquid state is between 90° to 105° C.

6. Method as claimed in claim 5, wherein the quantity of steam passed through the trifluralin in the liquid state is between 2 and 4 times the weight of the trifluralin.

7. Method as claimed in claim 3, wherein the solvent is a hydrocarbon or a halogenated hydrocarbon.

8. Method as claimed in claim 3, wherein the solvent is a ketone or an aldehyde.

* * * * *

UNITED STATES PATENT AND TRADEMARK OFFICE
CERTIFICATE OF CORRECTION

PATENT NO. : 4,876,388
DATED : October 24, 1989
INVENTOR(S) : Guido RAVETTA

It is certified that error appears in the above-identified patent and that said Letters Patent is hereby corrected as shown below:

Cover Page:

[54], line 2, "TRIFURALINE" should be -- TRIFLURALIN --;

Column 1, Title, "TRIFURALINE" should be -- TRIFLURALIN --;

Column 1, LINE 43, "tri-fluraline " should be -- tri-fluralin --;

Column 3, line 56, insert -- , -- after "however";

Claims:

Column 6, line 7, "1" should be -- 2 --.

Signed and Sealed this

Fourth Day of June, 1991

Attest:

HARRY F. MANBECK, JR.

Attesting Officer  Commissioner of Patents and Trademarks